(12) United States Patent
Spiro et al.

(10) Patent No.: US 6,288,043 B1
(45) Date of Patent: *Sep. 11, 2001

(54) INJECTABLE HYALURONATE-SULFATED POLYSACCHARIDE CONJUGATES

(75) Inventors: Robert C. Spiro, Half Moon Bay; LinShu Liu, Sunnyvale, both of CA (US)

(73) Assignee: Orquest, Inc., Mountain View, CA (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/336,005

(22) Filed: Jun. 18, 1999

(51) Int. Cl.⁷ .................. A61K 31/715; C08B 37/00; A61F 2/00

(52) U.S. Cl. .................. 514/54; 514/56; 514/59; 514/62; 536/53; 536/122; 536/123; 536/123.1; 536/124; 424/423; 424/426; 424/488

(58) Field of Search .................. 514/54, 56, 59, 514/62; 536/53, 122, 123, 123.1, 124; 424/423, 426, 488

(56) References Cited

U.S. PATENT DOCUMENTS

| | | | |
|---|---|---|---|
| 3,706,633 | * 12/1972 | Katchalski et al. | 435/178 |
| 4,582,865 | 4/1996 | Balazs et al. | 524/29 |
| 5,011,918 | * 4/1991 | Billmers et al. | 536/18.7 |
| 5,128,326 | * 7/1992 | Balazs et al. | 514/54 |
| 5,942,499 | * 8/1999 | Radomsky | 514/54 |

FOREIGN PATENT DOCUMENTS

| | | |
|---|---|---|
| 2752843 | 3/1998 | (FR) . |
| 98/08897 | * 3/1998 | (WO) . |
| WO 99/01143 | 1/1999 | (WO) . |
| PCT/US00/16793 | 6/2000 | (WO) . |

OTHER PUBLICATIONS

Miyamoto et al., Clin. Orthop. Red. Res., 274:266, May 1992.
Bitter et al., "A Modified Uronic Acid Carbazole Reaction", Anal. Biochem., 4:330–334, 1962.
Bubnis et al., "The Determination of Amino Groups in Soluble and Poorly Soluble Proteinaceous Materials", Anal. Biochem., 207:129–133, 1992.
Lin–Shu Liu et al., "An osteoconductive collagen/hyaluronate matrix for bone regeneration", Biomaterials, 20:1097–1108, 1999.
Cory et al., "Use of an Aqueous Soluble Tetrazolium/Formazan Assay for Cell Growth Assays in Culture", Cancer Commun., 3:207, 1991.
"Poly –hydroxy acid carrier for delivering recombinant human bone morphogenic protein–2 for bone regeneration", J. Control.Release., 39:287, 1996.
Lin–Shu Liu et al., "Controlled release of interleukin–2 for tumour immunotherapy using alginate/chitosan porous micropheres", J. Control. Release., 43:65–74, 1997.
Holinger et al., "Factors for Osseous Repair and Delivery: Part 1", J. Craniofac. Surg. 4:115, 1993.
Kenley et al., "Biotechnology and Bone Graft Substitutes", Pharm. Res. 10:1393, Oct. 1993.
Nakagawa et al., "Extracellurar Matrix Organization Modulates Gibroblast Growth and Growth Factor Responsiveness", Exp. Cell Res. 182:572, Jun. 1989.
Robinson et al., "Regenerating Hyaline Cartilage in Articular Defects of Old chickens Using Implants of Embryonal Chick Chondrocytes Embedded in a New Natural Delivery Substance", Calcif. Tissue Int., 46:246, Apr. 1990.
Sampath et al., "Recombinant Human Osteogenic Protein–1 Induces New Bone Formation in Vivo with a Specific Activity Comparable with Natural Bovine Osteogenic Protein and Stimulates Osteoblast", J.Biol. Chem., 267:20352, Oct. 1992.
Vlodavsky et al., "Endothelial cell–derived basic fibroblast growth factor: Synthesis and deposition into subendothelial extracellular matrix", PNAS, 84:2292, Apr. 1987.
Wozney et al., "Novel Regulators of Bone Formation: Molecular Clones and Activities", Science, 242:1528, Dec. 1988.
Anderson et al., "Recent advances in methods for inducing bone formation" Curr. Opin. Ther. Patents, 4:17 1994.
Liu, Lin–Shu (1/1999) "An osteoconductive collagen/hyaluronate matrix for bone regeneration" Biomaterials, Elsevier Science publishers, Barking, GB, vol. 20, pp. 1097–1108.

* cited by examiner

Primary Examiner—Kathleen K. Fonda
(74) Attorney, Agent, or Firm—Fish & Richardson, PC

(57) ABSTRACT

An injectable composition is provided for promoting bone and/or cartilage growth comprising hyaluronic acid cross-linked to sulfated polysaccharide through linking groups. The linking groups are diamines or amino polyalkylene glycols. The sulfated polysaccharide binds growth factors suitable for promoting tissue growth at the site of application of the composition.

24 Claims, 3 Drawing Sheets

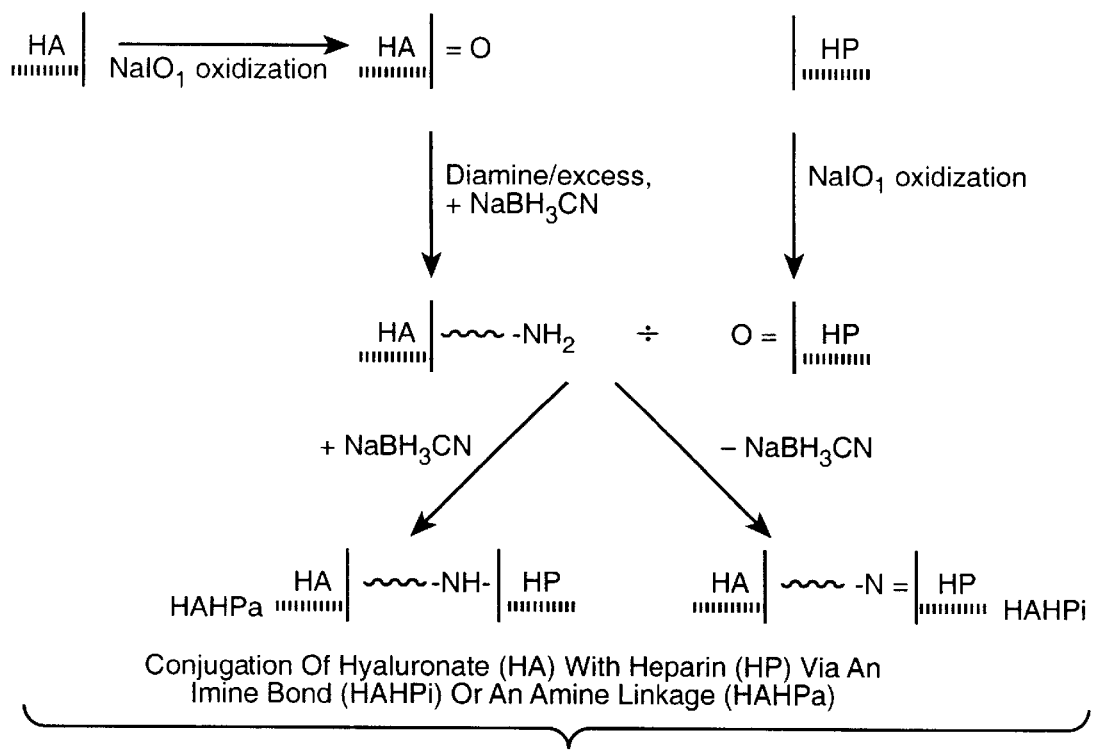
FIG._1
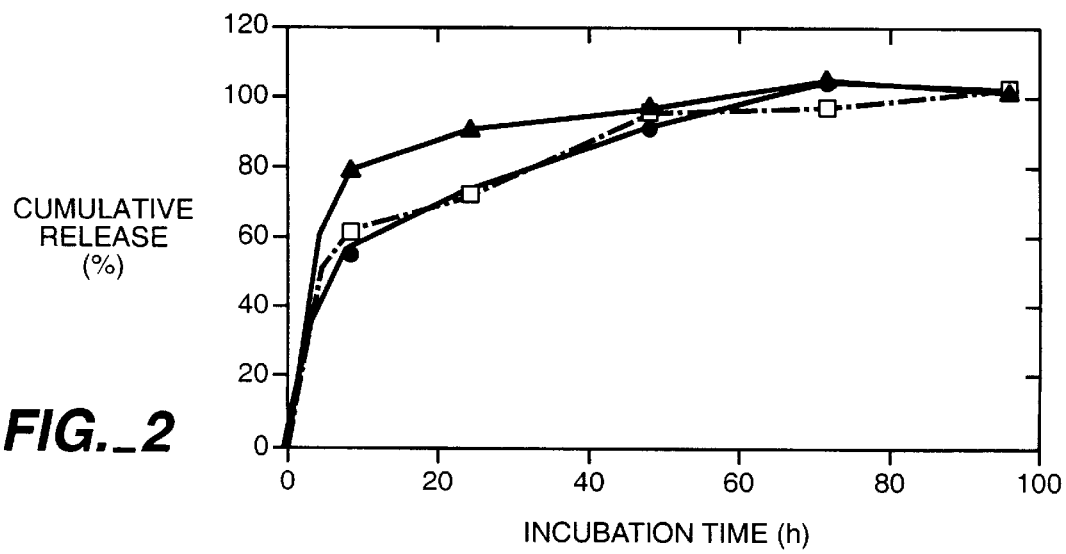
Cumulative Release Of FGF-2 From HAHPa (Circle), HAHPi (Square), And HA (Triangle).
FIG._2

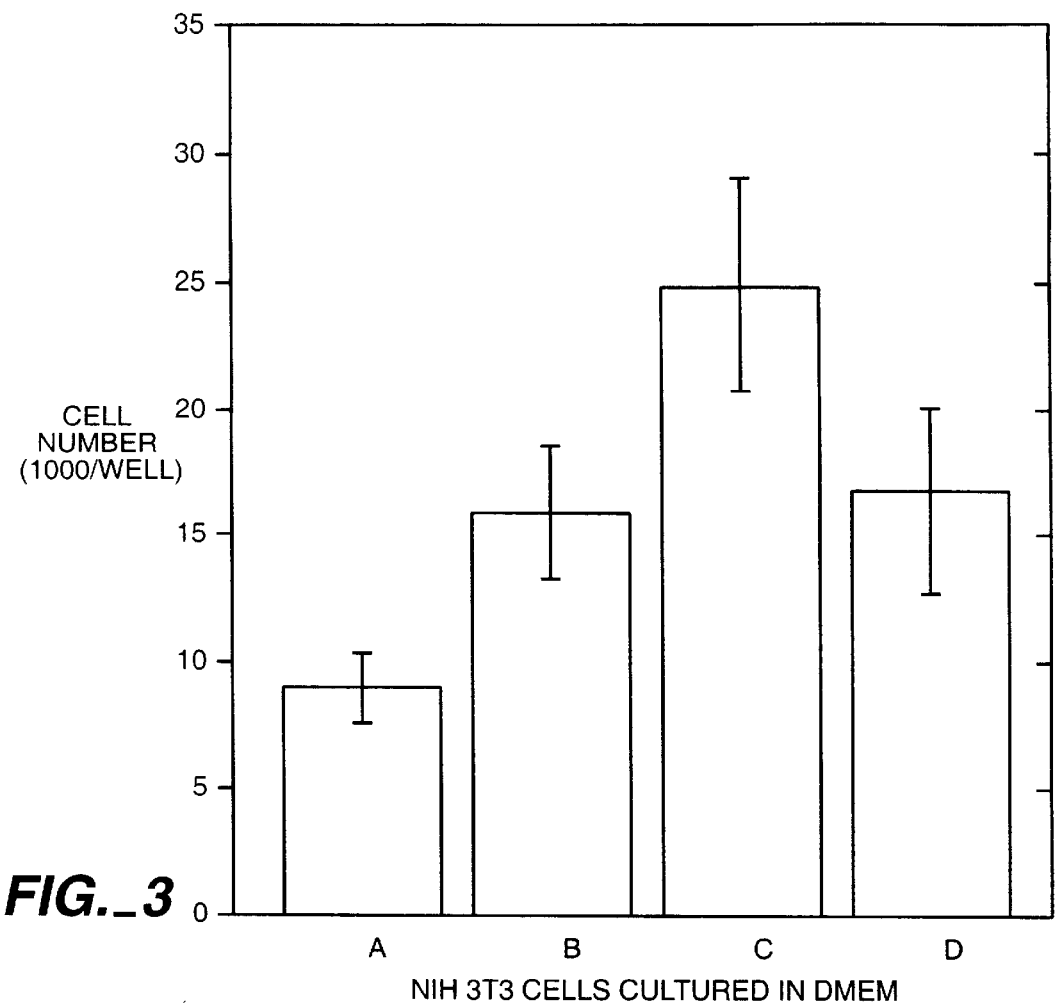
FIG._3
NIH 3T3 CELLS CULTURED IN DMEM
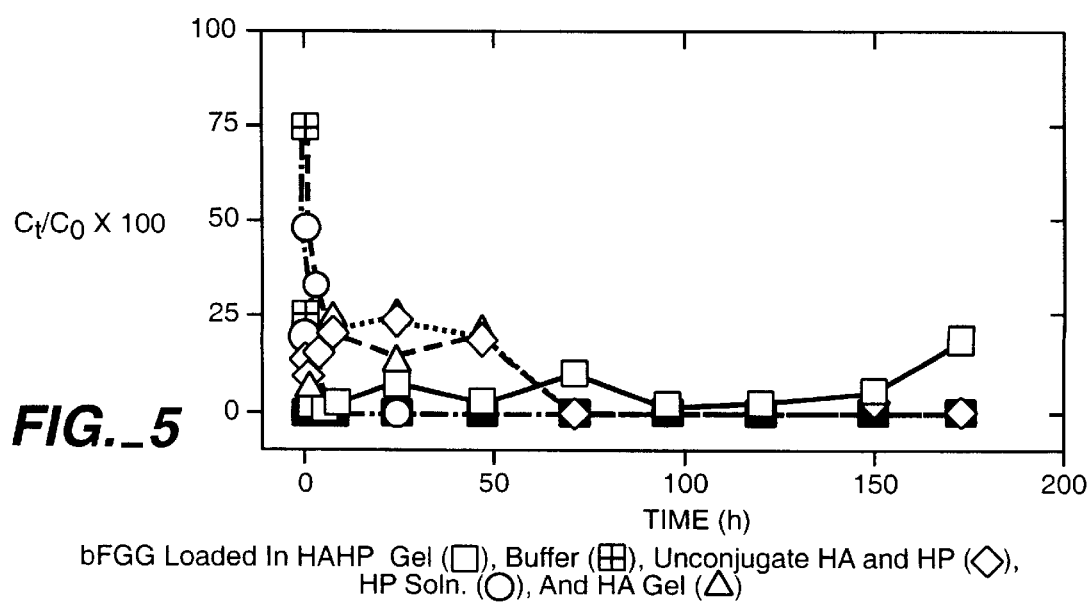
FIG._5
bFGG Loaded In HAHP Gel (□), Buffer (⊞), Unconjugate HA and HP (◇), HP Soln. (○), And HA Gel (△)

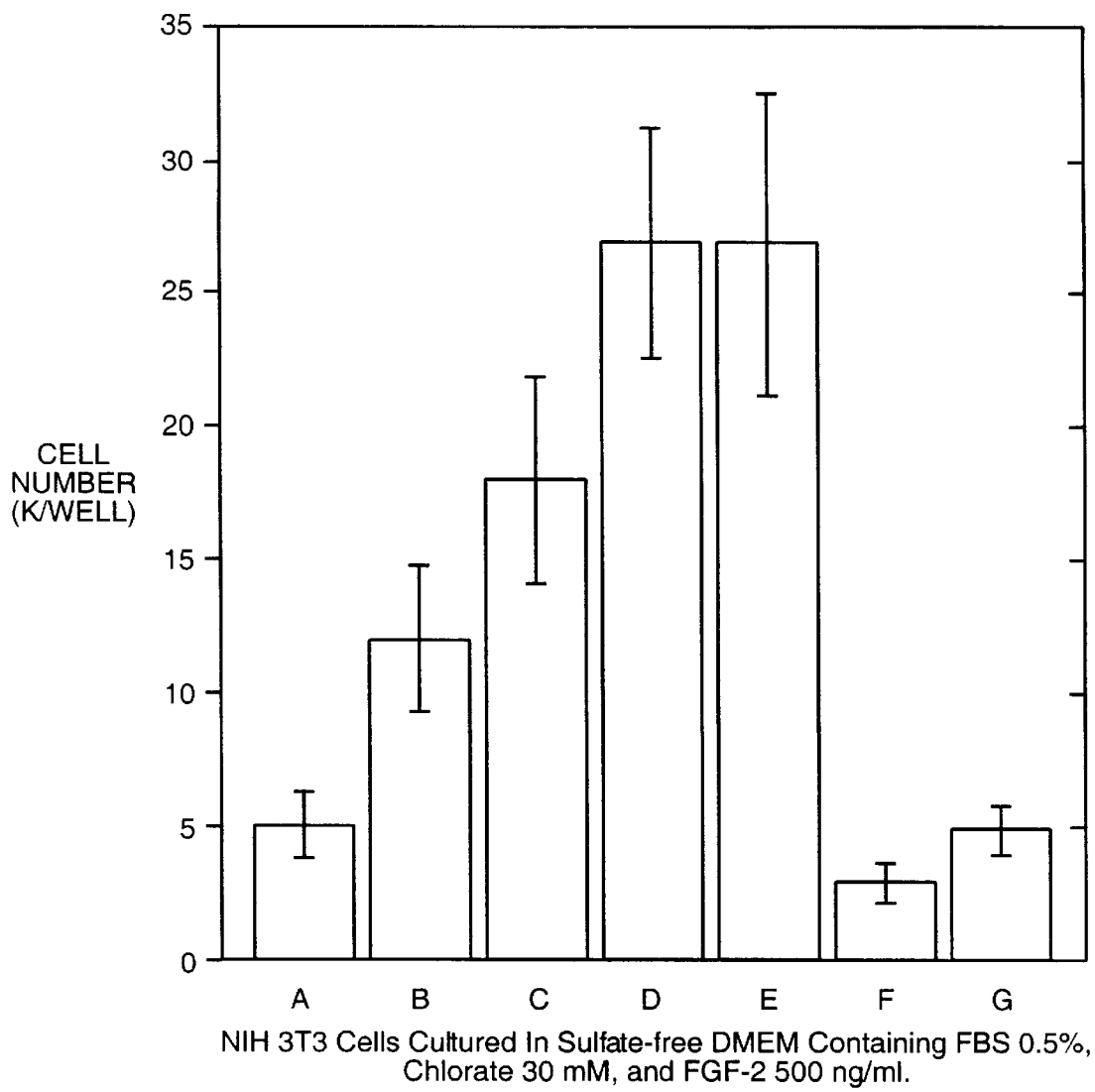
FIG._4

INJECTABLE HYALURONATE-SULFATED POLYSACCHARIDE CONJUGATES

The present invention is directed to an injectable composition for the therapeutic repair of bone cartilage tissue, methods of producing such compositions and methods of using it to promote tissue growth.

In particular, the invention is directed to an injectable gel which binds growth, differentiation and other factors to induce cell proliferation and differentiation in vitro or in vivo at a desired site of bone or cartilage growth.

BACKGROUND OF THE INVENTION

The development of therapeutic products to restore or replace the function of impaired connective tissues has been stimulated by an aging population, bone donor scarcity and the potential of transmission of infectious diseases. Due to the self-regenerative capacity of bone and cartilage, there has been extensive research into the development of biomaterials which support tissue induction from of repairative tissue surrounding tissue.

One approach to tissue repair involves the administration of growth factors in solution with an appropriate delivery system at the desired tissue site. See Kenley et al., Pharm. Res. 10:1393 (1993); Anderson et al., Curr. Opin. Ther. Patents, 4:17 (1994). A primary inducer of mesoderm formation in embryogenesis, bFGF, apparently plays a role in osteogenesis. Bone morphogenic proteins (BMPs), members of the transforming growth factor superfamily of proteins, are bone inducers. Sampath et al., J. Biol. Chem., 267:20352 (1992); Wozney et al., Science, 242:1528 (1988). These molecules are involved in cell proliferation and differentiation both in vitro and in vivo. The biological functions of these growth factors are mediated by the interaction of the growth factors with high-affinity cell-surface receptors and subsequent alterations in gene expression within the stimulated cells.

However, development of effective delivery systems for these growth factors has been a major obstacle. The development of an effective and reliable delivery system is crucial to the viable use of growth factors in bone or cartilage repair. Synthetic polymeric prostheses, inorganic ceramics, hydrogels, and injectable vehicles from natural or synthetic polymers have been investigated with the intention of localizing and sustaining active agents at the administered site, but it has been difficult to create a delivery system that incorporates growth factor stability and optimal release profiles. See Hollinger et al., J. Craniofac. Surg. 4:115 (1993); J. Control. Red. 39:287 (1996); Miyamoto et al., Clin. Orthop. Red. Res., 274:266 (1992).

Hyaluronic acid is a natural component of the extracellular matrix of most tissues and is readily sterilized, is biodegradable and can be produced in a wide range of consistencies and formats. It is generally water-soluble, biocompatible and its resorption characteristics can be controlled by the manipulation of monomers. It is a linear polymer made up of repeating glycosaminoglycan (GAG) disaccharide units of D-glucuronic acid and N-acetylglycosamine in β(1-3)and β(1-4) linkages.

Sulfated GAGs, such as dermatan sulfate, heparan sulfate, chondroitin sulfate and keratan sulfate are found mostly in the extracellular matrix and on the cell surface as proteoglycans. These macromolecules are secreted by cells and play a role in both signal transduction and storage of some growth factors such as FGFs, TGF-βs and BMPs. See Viodavsky et al., PNAS, 84:2292 (1987); Nakagawa et al., Exp. Cell Res. 182:572 (1989). Hyaluronic acid and sulfated GAGs are easily sterilized, biodegradable, and can be produced in a wide range of consistencies and formats. See Robinson et al., Calcif. Tissue Int., 46:246 (1990).

SUMMARY OF THE INVENTION

The present invention is directed to an injectable composition for inducing tissue growth at a target bone or cartilage site comprising hyaluronic acid (HA) cross-linked to a sulfated polysaccharide (SP) through linkage groups. The linkage group is a preferrably diamine or amino-terminated polyalkylene glycol. The sulfated polysaccharides are organic sulfates such as heparin, dermatan sulfate, chondroitin sulfate, heparan sulfate, dextran sulfate, keratan sulfate, and similar sulfated polysaccharides such as hexuronyl hexosaminoglycan sulfate, inositol hexasulfate and sucrose octasulfate which have a binding affinity for growth factors.

Methods are provided for producing such compositions by oxidizing hyaluronic acid under conditions such that aldehyde groups are formed on the hyaluronic acid, then reacting the oxidized hyaluronic acid with the amino-terminated linking group. The oxidized sulfated polysaccharide also contains aldehyde groups and is reacted with the other amino end of the linking group to form the cross-linked composition.

Methods of using the injectable composition are also provided by mixing the cross-linked composition with one or more growth factors and injecting the mixture at a site of desired bone growth in a subject.

As used in the present application, repair is defined as growth of new tissue. The basic cellular properties involved in repair include adhesion, proliferation, migration and differentiation. By conduction, it is meant that the tissue grows by extension on existing cells of the same type.

BRIEF DESCRIPTION OF THE DRAWING

FIG. 1 is a scheme of synthesis of compositions of the invention.

FIG. 2 is a release profile of FGF-2 described in Example 3.

FIG. 3 is a graph of the bioactivity of the compositions of the invention against control for stimulation of fibroblast cell growth described in Example 4.

FIG. 4 is a graph of cell growth as a function of concentration as described in Example 4.

FIG. 5 is a release profile of a composition of the invention against various controls as described in Example 3.

DESCRIPTION OF THE PREFERRED EMBODIMENTS

A method of preparing an injectable composition of the present invention involves oxidizing sugar rings on hyaluronic acid to form formaldehyde end groups using, for example, sodium or potassium periodate as a selective oxidizing agent. The amount of aldehyde groups produced in this manner can be stoichiometrically controlled. Typically from about one to 50% of the rings can be opened in this manner on a hyaluronic acid molecule. The aldehyde groups are then reacted with a diamine cross-linking group. In the presence of a reducing agent a secondary or tertiary amine is formed bridging the linking group to the hyaluronic acid. The sulfated polysaccharide is similarly prepared to oxidize sugar rings to form aldehyde groups. The oxidized sulfated polysaccharide is then reacted in the presence or absence of a reducing agent with the hyaluronic acid bearing the linking group to form a cross-linked hyaluronic acid-sulfated polysaccharide conjugate. In the absence of a reducing agent, the aldehyde and an amine group of the cross-linking group condense to form an imine.

We have discovered that growth factors, such as bFGF, can bind specifically to hyaluronate-heparin conjugate gels (HAHP), as well as other hyaluronate-sulfated polysaccharide gels (HASP), where heparin was coupled to hyaluronate via a labile imine bond. The binding of bFGF to HAHP, for example, is reversible and the release of bFGF from the gel occurs in a controlled manner that is dependent on the density of gel and the amount of heparin conjugated on the gel. While not intending to be bound by a theory, the release of a more active bFGF/heparin complex from HASP gels may be part of the mechanism by which bFGF stimulates cell proliferation and tissue augmentation. Other parameters such as the exchange absorption of growth factors between the gels and autogenous heparin or other components of extracellular matrix existing in the wound fluid of damaged tissue, may also play a significant role.

Typically the molecular weight of the hyaluronic acid in the sulfated polysaccharide will be in the range of about 1,000 to 10,000,000 daltons.

The preferred sulfated polysaccharides are heparin and heparan sulfate.

Besides heparin and heparan sulfate, gels formed from the conjugation of hyaluronate and sulfated glycosaminoglycans or sulfated organics such as dermatan sulfate, chondroitin sulfate, hexuronyl hexosaminoglycan sulfate, keratan sulfate, inositol hexasulfate and sucrose octasulfate also potentiate the mitogenic activity and stability of bFGF. Other growth factors such as those of the insulin-like growth factor family, the EGF family, the FGF family, the GDF family, the transforming growth factor-$\beta$s (TGF-$\beta$s) and its related superfamily of growth factors (e.g., BMPs) which bind to either heparin, heparan sulfate, or other sulfated glycosaminoglycans are also useful.

The reagents for opening sugar rings on the hyaluronic acid and sulfated polysaccharide may be any selective oxidizing agent which oxidizes the terminal hydroxyl group to an aldehyde, such as potassium or sodium periodate. Other reagents include specific sugar oxidases.

Referring to FIG. 1, there is shown a synthesis scheme for preparation of the conjugates. The hyaluronic acid (HA) is oxidized with sodium periodate to form aldehydes (HA=O). This is then reacted with the diamine linking group in presence of a reducing agent to form HA which is amine-linked to ends of the linking group. The heparin (HP) is similarly oxidized with sodium periodate to form aldehydes (HP=O). The HA containing the linking group is then reacted with the oxidized heparin (HP=O), in the presence or absence of a reducing agent, to form, respectively, the amine-linked conjugate, HAHPa, or the imine-linked conjugate, HAHPi.

While not intending to be bound by a theory, it is believed that the hyaluronic acid imparts primarily the property of viscosity for making the composition injectable and retainable at the desired site of tissue growth. Preferably, the hyaluronic acid will have a molecular weight in the range of about 1 to 2×10$^6$ daltons which is sufficient to provide the desired viscosity.

The linking agent may be hydrophobic, hydrophilic or have a long or short chain. Typically these will have the following formulas:

$H_2N(CH_2)_nNH_2$; n=1 to 1000
$H_2N(CH_2)_r[O(CH_2)_s]_tO(CH_2)_uNH_2$;
r, s, u are 1 to about 10;
t is 1 to about 100

While the linking agent is presumed to affect to some extent the viscosity and hydrophilicity of the injectable gel, it also has an effect on the activity and enzymatic stability of the conjugated sulfated polysaccharide. Preferred cross-linking groups are ethylenediamine, hexanediamine, dodecandiamine, and diamine-polyethylene glycol (PEG-(amine$_2$), typically with a molecular weight of about 1,000 to 6,000 daltons.

The sulfated polysaccharide will have specific or nonspecific binding capability to the growth factor.

Growth factors may be loaded into HASP gels simply by mechanical mixing the two parts at room temperature. Typically, bFGF in 9(w/v) sucrose, 1 mm EDNA, 20 mm sodium citrate buffered at pH 5.0, and GDF-5 in 20 mM acetic acid, pH 4 may be used. In a typical formulation, 50 $\mu$l of growth factor solution with known amount GF (10 ng–5 mg/ml) is mixed with 950 $\mu$l of the gel dissolved in corresponded buffer at the density of 5–20 mg/ml in a polypropylene microfuge tube at room temperature. Since the absorption of protein into polypropylene is negligible, the growth factor content in HASP gels is considered as the initial amount of growth factors added.

The proportion of hyaluronic acid to sulfated polysaccharide in the composition may be characterized on a molar or weight ratio basis. Typically the ratio by weight of hyaluronic acid to sulfated polysaccharide is from 99:1 to 1:99. This represents an approximate molar ratio of 99.9:0.1 to 1:9 respectively, assuming an average molecular weight of 10$^6$ daltons for hyaluronic acid and 10$^5$ daltons for the sulfated polysaccharide. The molar ratio may vary depending on the actual molecular weight of the sulfated polysaccharide and hyaluronic acid which are used.

The compositions are formed as a viscous gel and may either be directly applied or injected onto a site where the growth of new bone tissue is desired, such as for the filling of bone defects, fracture repair or grafting periodontal defects.

As will be understood by those with skill in the art, the amount of gel to be administered to conduct bone growth depends upon the extent of the bone defect to be treated. The following examples are provided for purposes of illustration and are not intended to limit the invention in any way.

EXAMPLE 1

Synthesis of Active Polysaccharide

Gels were formed by the conjugation of HA carrying primary amine groups with heparin (HP) carrying active aldehyde groups as shown in FIG. 1. The imine linked gels are identified as HAHPi and the amine linked gels are identified as HAHPa in Table 1. Polysaccharides carrying active aldehydes were prepared by oxidization with sodium periodate as described previously (*Biomaterials*, 20: 1097–1108, 1999). The degree of oxidization was controlled by altering the reaction time and was monitored by measuring the incorporation of 14C-methylamine. The concentration of aldehydes thus generated was calculated based on the specific radioactivity of 14C-methylamine labeled polysaccharides found in gel filtration void volume fractions. Primary amine groups were introduced into oxidized HA by reaction with an excess of ethylenediamine (—CHO/—NH$_2$,=1/60, mol/mol), and were quantitated using a trinitrophenylation reagent (*Anal. Biochem.*, 207:129–133, 1992).

The conjugation of HA to heparin was confirmed by Fourier-transform infrared spectroscopy (FT-IR) and fast protein liquid chromatography (FPLC) analysis. Heparin content was determined by an X-ray fluorescence method utilizing HA and heparin mixtures of known concentrations as standards.

TABLE 1

Characteristics of hyaluronate/heparin conjugate (HAHP)

| Samples number | Oxidized disaccharides in HA (%) | —$NH_2$ introduced into HA ($\mu$M/g) | HP content in HAHP (%) | Viscosity [$\eta$]***, (ml/mg) |
|---|---|---|---|---|
| 1) HAHPa | 2.18 ± 0.03 | 66.4 ± 3.2 | 15.8* | 189 |
| 2) HAHPa | 11.0 ± 0.12 | 141.4 ± 7.1 | 24.0* | 74 |
| 3) HAHPi | 2.18 ± 0.03 | 66.4 ± 3.2 | 15.8** | 185 |
| 4) HAHPi | 11.0 ± 0.12 | 141.4 ± 7.1 | 24.0** | 81 |

*determined by X-ray fluorescence analysis; calculated based on the amount of heparin added and the amount of total hyaluronate and heparin; *[$\eta$] = ($\eta_{sp}/C)_{C-1)}$, using D.I. water as a solvent $\eta$ and $\eta_0$ were measured at 25° C. using a viscometer.

EXAMPLE 2

Incorporation of FGF-2 into Gels

The FGF-2 (Scios, Inc., Mountain View, USA) was loaded into gels of Example 1 just prior to use by mixing at room temperature. $^{125}$I-labeled FGF-2 was used as a tracer for the release kinetics experiments and was mixed with unlabeled growth factor and HAHP gel in 9(w/v)sucrose, 1 mm EDNA, 20 mm sodium citrate buffered at pH 5.0. For the activity and stability studies, 0.2% collagen, 50 mm HCl at pH 4.0 was used as a solvent

EXAMPLE 3

Controlled Release of FGF-2 from Gels

Release tests were performed by a method described previously (*J. Control. Red.*, 43:65–74, 1997) using a six well tissue-culture plate equipped with a porous membrane insert (pore size, 0.4$\mu$,). Gel samples were loaded on the top of the membrane, and 5.0 ml of release medium (9% (w/v) sucrose, 1 mm EDNA, 20 mm sodium citrate buffered at pH 5.0) was added into the lower chamber. At the desired time points, the volume of media remaining in the chambers was calculated and the amount of FGF-2 released into the medium was quantified by scintillation counting. The amount of polysaccharides retained and released were measured using a previously described uronic acid assay (*Anal. Biochem.*, 4:330–334, 1962).

The cumulative release of FGF-2 from the amine linked and imine linked gels compared to HA is shown in FIG. 2 at concentrations of 1 mg/ml FGF-2 and 10 mg/ml gel. Release was retarded in the gels compared to release in HA.

FIG. 5 shows the release profile of bFGF from various HA, HP and HAHP combinations. Release is given as $C_t/C_o \times 100$, where $C_t$ is the amount of bFGF in the release medium and $C_o$ is the original amount of bFGF. The data is given as the mean with standard deviation (n=5). Incorporation of bFGF into the HAHP conjugate resulted in a more sustained growth fact r release profile when compared to either HA gel, HP in buffer, buffer alone (sucrose/EDTA/citrate, pH 5), or unconjugated HA and HP combinations. In the absence of conjugation of the HA and HP components, the release profile of bFGF was proportional to the viscosity of the carrier solution.

EXAMPLE 4

Effect of HAHP on FGF-2 Bioactivity and Stability

The bioactivity of FGF-2 in various formulations was measured by quantifying the stimulation of fibroblast cell growth in vitro. NIH 3T3 cells were cultured in either DMEM containing 10% (v/v) fetal bovine serum (FBS) or sulfate-free DMEM containing 0.5% FBS for three days under standard conditions. FGF-2 and HAHP were added at the desired ratios at the time of cell seeding. Cell number was measured using a MTS/PMS reagent (*Cancer Commun.*, 3:207, 1991). The results are shown in FIG. 3. Sample A was the control. In samples B through D, 500 ng/ml FGF-2 was added. In Sample C, 1.0 $\mu$g/ml. of HAHPi was also added. In Sample D, 1.0 $\mu$g/ml. of HAHPa was also added. In FIG. 4, increasing concentrations of HAHPi was added in Samples B through F at 0.6, 1.2, 2.0, 10 and 100 $\mu$g/ml, respectively. HAHPa (2 $\mu$g/ml.) was added in Sample G. Sample A was the control.

For the evaluation of growth factor stability, both FGF-2 in solution or incorporated into HAHP conjugate gels was incubated at 37° C. for 1, 3, 7, and 14 days in polypropylene tubes pre-coated with BSA. At each time point, an aliquot from each sample was removed and the activity of FGF-2 was assessed as described above. The results are in Table 2.

TABLE 2

Recovery of bFGF mitogenic activity after incubating at 37° C.

| Formulations | Recovery (%) | | | |
|---|---|---|---|---|
| | 1 day | 3 days | 1 week | 2 weeks |
| bFGF in collagen soln. | 6.2 ± 0.7 | 0 | N/A | N/A |
| bFGF in collagen soln. Containing heparin | 17.9 ± 1.1 | 12.5 ± 2.4 | 4.5 ± 0.3 | 0 |
| bFGF in collagen soln. Containing HAHPi | 9.3 ± 0.4 | 8.4 ± 0.9 | 5.4 ± 1.2 | 6.5 ± 0.7 |
| bFGF in sucrose soln. | 1.9 ± 0.2 | 0 | N/A | N/A |
| bFGF in sucrose soln. Containing heparin | 4.5 ± 0.1 | 0 | N/A | N/A |
| bFGF in sucrose soln. Containing HAHPi | 2.4 ± 0.1 | 0 | N/A | N/A |

The Concentrations of bFGF, heparin, and HAHPi in all formulatiions were 1.0 mg, 350 $\mu$g, and 2.2 mg per ml, respectively. Heparin content in HAHPi was 16%. Collagen solution: 2.0 mg collagen in 50 mM HCl. Sucrose solution: 9% sucrose, 1 mM EDTA, 30 mM sodium acetate (pH 5.0). After incubating at 37° C. for desired time period, each formulation was diluted to 1000 times with PBS containing 0.2% collagen (pH 7.0). 10 $\mu$l of the diluted solution were added to NIH 3T3 cell cultures (5 × 10$^3$ cells/well) in 24 well tissue-culture plate in the presence of 2.0 ml DMEM supplemented with 10% FBS. After 3 days in culture, the medium was replaced by 2.0 ml fresh DMEM, and the cell number was counted by MTS/PMS method. Recovery of bFGF was compared to that without pre-incubation. Experiments were triplicate.

EXAMPLE 5

Animal Model and in vivo Evaluation

The effect of HAHP gels containing FGF-2 on periosteal bone formation was examined in Sprague-Dawley rats (4–6 weeks old, 140–160 g, male). 50 $\mu$l aliquots of gel formulations containing FGF-2 (10 ng to 1.0 mg per ml), or control carrier solution were injected into pockets created under the periosteum of the parietal bone of the rats. Animals were sacrificed tier 14 days, and excised calvaria were fixed with 10% neutral formalin, decalcified, and embedded in paraffin. Coronal sections (3–5 $\mu$m thick) were prepared and stained with hermatoxylin and eosin for light microscopic evaluation. The thickness of the parietal bone (excluding the thickness of the periosteum) was measured using photographic images captured with a video camera. Sections were calibrated with a stage micrometer at three separate points, approximately 500 μm apart. The average value was calculated and used as the mean thickness of each parietal bone.

Statistical significance of the data was evaluated by unpaired t-test. The results are shown in Table 3.

TABLE 3

Formulation-dependent effect of bFGF on parietal bone thickness

| Samples | Thickness, μm |
|---|---|
| HAHPi/FGF-2 | 660 ± 77 |
| FGF-2/Buffer | 294 ± 13 |
| HA/FGF-2 | 283 ± 36 |
| HAHPi | 309 ± 34 |

What is claimed is:

1. An injectable composition for promoting tissue growth at a target bone or cartilage site comprising hyaluronic acid cross-linked through linking groups to a sulfated polysaccharide wherein said linking groups are selected from the group consisting of diamines and diamine-polyalkylene glycols.

2. A composition according to claim 1 wherein said composition is a water-soluble, viscous gel.

3. A composition according to claim 1 wherein said sulfated polysaccharide is selected from the group consisting of heparin, chondroitin sulfate, dextran sulfate, dermatan sulfate, heparan sulfate, keratan sulfate, hexuronyl hexosaminoglycan sulfate, inositol hexasulfate, and sucrose octasulfate.

4. A composition according to claim 1 wherein said linking group is selected from the group consisting of ethylenediamine, hexanediamine, dodecandiamine, and diamine-polyethylene glycol.

5. A composition according to claim 4 wherein the molecular weight of said linking group is in the range of about 1,000 to 6,000 daltons.

6. A composition according to claim 1 wherein the molecular weight of said hyaluronic acid is in a range of 1 to $2 \times 10^6$ daltons.

7. A composition according to claim 1 wherein the molecular weight of said sulfated polysaccharide is less than about $10^4$ daltons.

8. A composition according to claim 1 wherein said hyaluronic acid is bonded to said linking group by an amine.

9. A composition according to claim 1 wherein said sulfated polysaccharide is bonded to said linking group by an amine or imine.

10. A composition according to claim 1 further comprising a growth factor.

11. A method for preparing an injectable gel to support the repair of bone or cartilage comprising the steps of oxidizing hyaluronic acid to form a modified hyaluronic acid having aldehyde groups, reacting said modified hyaluronic acid with a linking agent having amine end groups to form a hyaluronic acid having pendant linking groups with terminal amine groups, and reacting said hyaluronic acid having pendant linking groups with a modified sulfated polysaccharide having aldehyde groups to covalently link said sulfated polysaccharide to said linking groups.

12. A method for inducing the growth of bone or cartilage tissue in vivo comprising the step of administering an injectable composition comprising a composition according to claim 1 and a growth factor at a site of desired tissue growth.

13. A method according to claim 12 wherein said linking group is selected from the group consisting of ethylenediamine, hexanediamine, dodecandiamine, and diamine-polyethylene glycol.

14. A method according to claim 12 wherein the molecular weight of said linking group is in the range of about 1,000 to 6,000 daltons.

15. A method according to claim 12 wherein the molecular weight of said hyaluronic acid is in a range of 1 to $2 \times 10^6$ daltons.

16. A method according to claim 12 wherein the molecular weight of said sulfated polysaccharide is less than about $10^4$ daltons.

17. A method according to claim 12 wherein said hyaluronic acid is bonded to said linking group by an amine.

18. A method according to claim 12 wherein said sulfated polysaccharide is bonded to said linking group through an amine or imine.

19. A composition according to claim 3 wherein said sulfated polysaccharide comprises heparin.

20. A composition according to claim 10 wherein said growth factor is selected from the group consisting of the IGF, TGF-β, BMP, EGF, FGF and GDF families of factors.

21. A composition according to claim 20 wherein said growth factor comprises an FGF.

22. A method according to claim 12 wherein said sulfated polysaccharide comprises heparin.

23. A method according to claim 12 wherein said growth factor is selected from the group consisting of the IGF, TGF-β, BMP, EGF, FGF and GDF families of factors.

24. A method according to claim 23 wherein said growth factor comprises an FGF.

* * * * *